United States Patent
Woo et al.

(10) Patent No.: US 10,251,957 B2
(45) Date of Patent: Apr. 9, 2019

(54) COMPOSITION FOR TREATING DIABETES COMPRISING LONG-ACTING INSULIN CONJUGATE AND LONG-ACTING INSULINOTROPIC PEPTIDE CONJUGATE

(75) Inventors: Young Eun Woo, Daejeon (KR); Myung Hyun Jang, Seoul (KR); Young Jin Park, Suwon-si (KR); Young Kyung Park, Hwaseong-si (KR); Chang Ki Lim, Hwaseong-si (KR); Se Chang Kwon, Seoul (KR)

(73) Assignee: HANMI SCIENCE CO., LTD., Hwaseong-si (KR)

( * ) Notice: Subject to any disclaimer, the term of this patent is extended or adjusted under 35 U.S.C. 154(b) by 0 days.

(21) Appl. No.: 14/123,355

(22) PCT Filed: Jun. 1, 2012

(86) PCT No.: PCT/KR2012/004367
§ 371 (c)(1),
(2), (4) Date: Dec. 2, 2013

(87) PCT Pub. No.: WO2012/165915
PCT Pub. Date: Dec. 6, 2012

(65) Prior Publication Data
US 2014/0120120 A1    May 1, 2014

(30) Foreign Application Priority Data
Jun. 2, 2011 (KR) .................. 10-2011-0053488

(51) Int. Cl.
A61K 38/28 (2006.01)
A61K 38/00 (2006.01)
A61K 47/48 (2006.01)
A61K 38/26 (2006.01)
A61K 47/68 (2017.01)

(52) U.S. Cl.
CPC ........ *A61K 47/48415* (2013.01); *A61K 38/26* (2013.01); *A61K 38/28* (2013.01); *A61K 47/68* (2017.08); *A61K 47/6811* (2017.08); *A61K 47/6883* (2017.08)

(58) Field of Classification Search
None
See application file for complete search history.

(56) References Cited

U.S. PATENT DOCUMENTS

| | | | |
|---|---|---|---|
| 5,424,286 A | 6/1995 | Eng | |
| 8,476,230 B2* | 7/2013 | Song | C07K 14/605 424/195.11 |
| 2006/0275254 A1 | 12/2006 | Kim et al. | |
| 2007/0054851 A1 | 3/2007 | Lin et al. | |
| 2009/0202481 A1 | 8/2009 | Li et al. | |
| 2009/0221485 A1 | 9/2009 | James | |
| 2010/0105877 A1 | 4/2010 | Song et al. | |
| 2011/0020345 A1 | 1/2011 | Herring et al. | |
| 2011/0152185 A1* | 6/2011 | Plum | C07K 14/605 514/6.5 |
| 2011/0257091 A1* | 10/2011 | DiMarchi | C07K 14/62 514/6.2 |
| 2013/0028918 A1* | 1/2013 | Song | A61K 38/28 424/179.1 |

FOREIGN PATENT DOCUMENTS

| | | |
|---|---|---|
| CA | 2 747 490 A1 | 4/1918 |
| CN | 1635900 A | 7/2005 |
| CN | 101646451 A | 2/2010 |
| CN | 102046207 A | 5/2011 |
| JP | 2008-169195 A | 7/2008 |
| KR | 10-2004-0081378 A | 9/2004 |
| KR | 10-2005-0047032 A1 | 5/2005 |
| KR | 10-2006-0106486 A1 | 10/2006 |
| KR | 10-0725315 B1 | 7/2007 |
| KR | 10-2008-0064750 A1 | 7/2008 |
| KR | 10-2009-0008151 A1 | 1/2009 |
| KR | 10-2011-0111267 A1 | 10/2011 |
| KR | 10-2011-0134209 A1 | 12/2011 |
| KR | 10-2011-0134210 A1 | 12/2011 |
| WO | 03/035099 A1 | 5/2003 |
| WO | 2006/029634 A2 | 3/2006 |

(Continued)

OTHER PUBLICATIONS

Hu et al. 2001. NEJM. 345:790-797.*

(Continued)

*Primary Examiner* — Shulamith H Shafer
(74) *Attorney, Agent, or Firm* — Sughrue Mion, PLLC (57) ABSTRACT

The present invention relates to a composition for the prevention or treatment of diabetes comprising a long-acting insulin conjugate and a long-acting insulinotropic peptide conjugate, and a therapeutic method for the treatment of diabetes, and more particularly, concurrent administration of the long-acting insulin conjugate and the long-acting insulinotropic peptide conjugate inhibits weight gain caused by insulin treatment, and vomiting and nausea caused by insulinotropic peptide treatment, and reduces the required dose of insulin, thereby remarkably improving drug compliance. Moreover, each of the long-acting insulin conjugate and the long-acting insulinotropic peptide conjugate of the present invention is prepared by linking insulin or insulinotropic peptide with an immunoglobulin Fc region via a non-peptidyl linker, thereby showing improved in-vivo duration of efficacy and stability.

15 Claims, 3 Drawing Sheets
Specification includes a Sequence Listing.

(56) References Cited

FOREIGN PATENT DOCUMENTS

| WO | 2008/082274 A1 | 7/2008 |
|---|---|---|
| WO | 2009/069983 A2 | 6/2009 |
| WO | 2010/011096 A2 | 1/2010 |
| WO | 2010/043047 A1 | 4/2010 |
| WO | 2010/092125 A1 | 8/2010 |
| WO | 2010/092163 A2 | 8/2010 |
| WO | 2011/058083 A1 | 5/2011 |
| WO | 2011/122921 A2 | 10/2011 |
| WO | 2011/161161 A1 | 12/2011 |
| WO | 2012/011752 A2 | 1/2012 |
| WO | 2014/161837 A1 | 10/2014 |

OTHER PUBLICATIONS

Lindstrom et al. 2006. Lancet. 368:1673-1679.*
Gutniak et al. 1992. NEJM. 326:1316-22.*
Ohkubo et al. 1995. Diabetes Res. and Clin Pract. 28:103-117.*
International Searching Authority International Search Report for PCT/KR2012/004367 dated Dec. 27, 2012.
European Patent Office; Communication dated Feb. 16, 2015 in counterpart application No. 12792243.3.
Taiwanese Patent Office, Communication dated Mar. 20, 2014 issued in corresponding Taiwanese Patent Application No. 101119709.
Korean Patent Office, Communication dated Jul. 17, 2014 issued in corresponding Korean application No. 10-2012-0059464.
Japanese Patent Office, Communication dated Feb. 23, 2016 issued in counterpart application No. 2014-513450.
State Intellectual Property Office of the P.R.C., Communication dated Mar. 3, 2016 issued in counterpart application No. 201280026982.0.
Russian Federal Service for Intellectual Property Office, Communication dated Apr. 7, 2016 in counterpart Russian Application No. 2013152335/15.
Israel Patent Office, Communication dated Jun. 21, 2016 in counterpart Israel Application No. 229726.
Brom, Maarten et al., "$^{68}$Ga-labelled exendin-3, a new agent for the detection of insulinomas with PET", Eur J Nucl Med Mol Imaging, 2010, No. 37, pp. 1345-1355.
Ding, Xiaokun et al., "Exendin-4, a Glucagon-Like Protein-1 (GLP-1) Receptor Agonist, Reverses Hepatic Steatosis in ob/ob Mice", Hepatology, Jan. 2006, No. 43, vol. 1, pp. 173-181 (total 17 pages).
Hernández-Yero, Arturo et al., "Current pharmacological agents in the treatment of non-insulin-dependent diabetes mellitus", Rev. Cubana Med Gen Integr, 1997, vol. 13, No. 6, pp. 596-609 (total 25 pages).
Sheffield, C.A. et al., "Safety and Efficacy of Exenatide in Combination with Insulin in Patients with Type 2 Diabetes Mellitus", Endocrine Practice, Apr. 2008, vol. 14, No. 3, pp. 285-292.
Paisley, A. N. et al., "Stabilizing effect of exenatide in a patient with C-peptide-negative diabetes mellitus", Diabetic Medicine, 2009, vol. 26, pp. 935-938.
Nayak, U.A. et al., "Exenatide therapy in insulin-treated type 2 diabetes and obesity", Q J Med, 2010, vol. 103, pp. 687-694.
Lane, Wendy, M.D. et al., "The Effect of Liraglutide Added to U-500 Insulin in Patients with Type 2 Diabetes and High Insulin Requirements", Diabetes Technology & Therapeutics, 2011, vol. 13, No. 5, pp. 592-595.
Communication dated Jun. 24, 2016 from the Chilean Patent Office in counterpart Application No. 2013-003454.
Communication dated Jul. 12, 2016 from the Mexican Patent Office in counterpart Application No. MX/a/2013/014029.
Communication dated Aug. 9, 2016 from the Japanese Patent Office in counterpart Application No. 2014-513450.
Japanese Patent Office, Communication dated Feb. 7, 2017 issued in counterpart Japanese Application No. 2014-513450.
Canadian Intellectual Property Office; Communication dated Apr. 12, 2018 in counterpart Canadian application No. 2,837,856.
Satish K. Garg, M.D., "The Role of Basal Insulin and Glucagon-Like Peptide-1 Agonists in the Therapeutic Management of Type 2 Diabetes—A Comprehensive Review", Diabetes Technology & Therapeutics, vol. 12, No. 1, 2010, pp. 11-24, XP055419323.
Mexican Patent Office, Communication dated Jan. 15, 2018 in counterpart application No. MX/E/2017/075647.
Indian Patent Office, Communication dated Mar. 9, 2018 in counterpart application No. 10360/DELNP/2013.

* cited by examiner

SEQUENCE LISTING

```
<160> NUMBER OF SEQ ID NOS: 5

<210> SEQ ID NO 1
<211> LENGTH: 21
<212> TYPE: PRT
<213> ORGANISM: Artificial Sequence
<220> FEATURE:
```

-continued

<223> OTHER INFORMATION: alpha chain of insulin

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Artificial Sequence
<220> FEATURE:
<223> OTHER INFORMATION: beta chain of insulin

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: GLP-1(7-37)

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 39
<212> TYPE: PRT
<213> ORGANISM: Artificial Sequence
<220> FEATURE:
<223> OTHER INFORMATION: Exendin-3

<400> SEQUENCE: 4

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Exendin-4

<400> SEQUENCE: 5

His Gly Glu Gly Thr Phe Thr Ser Asp Leu Ser Lys Gln Met Glu Glu
1               5                   10                  15

```
Glu Ala Val Arg Leu Phe Ile Glu Trp Leu Lys Asn Gly Gly Pro Ser
            20                  25                  30
Ser Gly Ala Pro Pro Pro Ser
            35
```

COMPOSITION FOR TREATING DIABETES COMPRISING LONG-ACTING INSULIN CONJUGATE AND LONG-ACTING INSULINOTROPIC PEPTIDE CONJUGATE

CROSS REFERENCE TO RELATED APPLICATIONS

This application is a National Stage of International Application No. PCT/KR2012/004367 filed Jun. 1, 2012, claiming priority based on Korean Patent Application No. 10-2011-0053488 filed Jun. 2, 2011, the contents of all of which are incorporated herein by reference in their entirety.

TECHNICAL FIELD

The present invention relates to a composition for the prevention or treatment of diabetes comprising a long-acting insulin conjugate and a long-acting insulinotropic peptide conjugate, and a method for treating diabetes comprising the step of administering the composition.

BACKGROUND ART

Insulin is a peptide secreted by the beta cells of the pancreas, and plays an important role in controlling the blood glucose level in the body. A metabolic disease, diabetes is associated with elevated blood glucose levels caused by an abnormality in the secretion or function of insulin. Type 1 diabetes is caused by elevated blood glucose levels due to failure in insulin production of the pancreas, and type 2 diabetes is caused by elevated blood glucose levels due to an abnormality in the secretion or function of insulin. Patients with type 2 diabetes are usually treated with oral hypoglycemic agents having a chemical substance as a main ingredient, and in some cases, given with insulin, whereas patients with type 1 diabetes require insulin treatment.

The most common insulin therapy involves insulin injections before and/or after meals. Currently, injectable insulin is available, and as a general rule, is given in a subcutaneous injection. The method of administration varies depending on its time course of action. Insulin injection shows a more rapid hypoglycemic effect than oral administration, and can be safely used when oral administration is not possible. Also, there is no dose limit for insulin use. However, long-term use of insulin three times a day can lead to disadvantages such as aversion to needles, difficulty in handling the injection device, hypoglycemia, and weight gain. Weight gain due to long-term use of insulin may increase the risk of cardiovascular disease and insulin resistance. Meanwhile, there are many efforts being made to maximize the efficacy by maintaining the long term, elevated levels of insulin peptide drugs after absorption by the body. For example, long-acting insulin formulations such as Lantus (Insulin glargine; Sanofi Aventis) and Levemir (Insulin detemir; Novo Nordisk) have been developed and are commercially available. Unlike insulin NPH (Neutral Protamine Hagedorn), these long-acting drugs reduce the risk of hypoglycemia during sleep, and Levemir in particular was associated with somewhat less weight gain. However, these drug formulations are also disadvantageous in that they must be given once or twice a day.

Meanwhile, one insulinotropic peptide, glucagon like peptide-1 (GLP-1), is an incretin hormone secreted by L-cells of the ileum and colon. Glucagon like peptide-1 functions to augment insulin release in a glucose-dependent manner so as to prevent hypoglycemic episodes. Owing to this property, it received attention as a potential treatment for type 2 diabetes. However, the primary obstacle to the use of GLP-1 as a therapeutic agent is its extremely short half-life of less than 2 minutes in plasma. Currently, exendin-4 is commercially available as a glucagon like peptide-1 receptor agonist, and it is a glucagon like peptide-1 analogue purified from the salivary gland of a gila monster. Exendin-4 has resistance to DPP IV (Dipeptidyl peptidase-4), and higher physiological activity than glucagon like peptide-1. As a result, it had an in-vivo half-life of 2 to 4 hours, which was longer than that of glucagon like peptide-1 (U.S. Pat. No. 5,424,286). However, with the method for increasing the resistance to DPP IV only, the physiological activity is not sufficiently sustained, and for example, in the case of commercially available exendin-4 (exenatide), it needs to be injected to a patient twice a day, and exenatide-treated patients still experience adverse events such as nausea and vomiting.

In order to solve the above problems, the present inventors suggested a long-acting peptide conjugate, which was prepared by linking a physiologically active polypeptide and an immunoglobulin Fc region via a non-peptidyl polymer as a linker by a covalent bond, thereby sustaining the activity and improving the stability of the protein drug at the same time (Korean Patent No. 10-0725315). In particular, they found that each of the long-acting insulin conjugate and the long-acting exendin-4 conjugate exerts remarkably increased in-vivo efficacy (Korean Patent Application Nos. 10-2008-0001479 and 10-2010-0054068).

However, there are still the problems of weight gain, or nausea and vomiting, when insulin or exendin-4 is injected in an amount which maintains a stable blood glucose level. Thus, there is an urgent need to develop a therapeutic method showing excellent therapeutic effects on diabetes with lower doses and less frequent use of the drug.

DISCLOSURE

Technical Problem

The present inventors have made many efforts to develop a therapeutic agent for diabetes which has the long-lasting therapeutic efficacy and lowers adverse events such as nausea and vomiting at the same time. They attempted to perform concurrent administration of a long-acting exendin-4 conjugate and a long-acting insulin conjugate that stimulate a glucagon like peptide-1 receptor and an insulin receptor at the same time. As a result, they found that concurrent administration of the long-acting insulin conjugate and the long-acting exendin-4 conjugate improves in-vivo duration of efficacy and stability, and remarkably reduces the doses of the drugs, leading to a stable blood glucose level. In addition, they found that it improves the adverse events such as vomiting and nausea induced by glucagon like peptide-1 agonist and exendin-4 or derivatives thereof, and that the use of long-acting exendin-4 conjugate reduces weight gain caused by the use of insulin, thereby completing the present invention.

Technical Solution

An object of the present invention is to provide a pharmaceutical composition for the prevention or treatment of diabetes, comprising a long-acting insulin conjugate and a long-acting insulinotropic peptide conjugate.

Another object of the present invention is to provide a method for preventing or treating diabetes, comprising the step of administering the composition to a subject having diabetes or at risk of having diabetes.

Another object of the present invention is to provide a pharmaceutical composition for the prevention or treatment of diabetes comprising a long-acting insulin conjugate and an insulinotropic peptide.

Another object of the present invention is to provide a pharmaceutical composition for the prevention or treatment of diabetes comprising insulin and a long-acting insulinotropic peptide conjugate.

Advantageous Effects

The long-acting insulin conjugate and the long-acting exendin-4 conjugate of the present invention show excellent therapeutic effects on diabetes, and in particular, the concurrent administration thereof stimulates an insulin receptor and a glucagon like peptide-1 receptor at the same time to improve in-vivo duration of the efficacy and stability thereof, and to remarkably reduce the required doses of the drugs and stably control the blood glucose at a stable level, leading to improvements in hypoglycemia and weight gain. In addition, it inhibits nausea and vomiting and has improved drug compliance as a therapeutic agent for diabetes. In particular, it has remarkably improved stability and in-vivo duration of efficacy allowing a reduction in treatment frequency, which contributes to patient convenience.

BEST MODE

In one aspect, the present invention provides a pharmaceutical composition for the prevention or treatment of diabetes, comprising a long-acting insulin conjugate and a long-acting insulinotropic peptide conjugate. The composition of the present invention is characterized by concurrent administration of the long-acting insulin conjugate and the long-acting insulinotropic peptide conjugate.

As used herein, the term "long-acting insulin conjugate" means insulin linked with an immunoglobulin Fc region via a non-peptidyl linker.

The long-acting insulin conjugate of the present invention has an improved duration of in-vivo efficacy, compared to native insulin, and the long-acting insulin conjugate may include insulin prepared by modification, substitution, addition, or deletion of the amino acid sequences of the native insulin, insulin conjugated to a biodegradable polymer such as polyethylene glycol (PEG), insulin conjugated to a long-acting protein such as albumin or immunoglobulin, insulin conjugated to a fatty acid having the ability of binding to albumin in the body, or insulin encapsulated in biodegradable nanoparticles, but the type of the long-acting insulin conjugate is not limited thereto.

As used herein, the term "insulin"? means a peptide that is secreted by the pancreas in response to elevated glucose levels in the blood to take up glucose in the liver, muscle, or adipose tissue and turn it into glycogen, and to stop the use of fat as an energy source, and thus controls the blood glucose level. This peptide includes the native insulin, basal insulin, insulin agonists, precursors, derivatives, fragments thereof, and variants thereof.

The term, "Native insulin" is a hormone that is secreted by the pancreas to promote glucose absorption and inhibit fat breakdown, and thus functions to control the blood glucose level. Insulin is formed from a precursor having no function of regulating the blood glucose level, known as proinsulin, through processing. The amino acid sequences of insulin are as follows:

```
Alpha chain:
                                              (SEQ ID NO. 1)
Gly-Ile-Val-Glu-Gln-Cys-Cys-Thr-Ser-Ile-Cys-Ser- Leu-Tyr-Gln-Leu-Glu-Asn-Tyr-Cys-Asn Beta chain:
                                              (SEQ ID NO. 2)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

The term, "basal insulin" means a peptide that manage normal daily blood glucose fluctuations, for example Levemir, Glagine, Deglude etc.

The term, "insulin agonist" means a compound that binds to the insulin receptor to show the biological activity equal to that of insulin, which is irrelevant to the structure of insulin.

The term, "insulin variant" is a peptide having one or more amino acid sequences different from those of native insulin, and means a peptide that retains the function of controlling the blood glucose level in the body, and it may be prepared by any one of substitution, addition, deletion, and modification or by a combination thereof in a part of the amino acid sequences of the native insulin.

The term, "insulin derivative" means a peptide having at least 80% amino acid sequence homology with the native insulin, which may have some groups on the amino acid residue chemically substituted (e.g., alpha-methylation, alpha-hydroxylation), deleted (e.g., deamination), or modified (e.g., N-methylation), and has a function of regulating the blood glucose level in the body.

The term, "insulin fragment" means a fragment having one or more amino acids added or deleted at the N-terminus or the C-terminus of the native insulin, in which non-naturally occurring amino acids (for example, D-type amino acid) can be added, and has a function of regulating the blood glucose level in the body.

Each of the preparation methods for the agonists, derivatives, fragments, and variants of insulin can be used individually or in combination. For example, the present invention includes a peptide that has one or more amino acids different from those of the native peptide and deamination of the N-terminal amino acid residue, and has a function of regulating the blood glucose level in the body.

In a specific embodiment, the insulin used in the present invention may be produced by a recombination technology, and may also be synthesized using a solid phase synthesis method.

Further, the insulin used in the present invention is characterized in that a non-peptidyl polymer is linked to the amino terminus of the beta chain of insulin. This non-peptidyl polymer may be used as a linker in the present invention. The non-peptidyl polymer is linked as a linker, thereby maintaining the activity and improving the stability of insulin.

The term "non-peptidyl polymer", as used herein, refers to a biocompatible polymer including two or more repeating units linked to each other by any covalent bond excluding a peptide bond. In the present invention, the non-peptidyl polymer may be interchangeably used with the non-peptidyl linker.

The non-peptidyl polymer useful in the present invention may be selected from the group consisting of a biodegradable polymer, a lipid polymer, chitin, hyaluronic acid, and a combination thereof, and preferably, the biodegradable polymer may be polyethylene glycol, polypropylene glycol, ethylene glycol-propylene glycol copolymer, polyoxyethylatedpolyol, polyvinyl alcohol, polysaccharide, dextran, polyvinyl ethyl ether, polylactic acid (PLA) or polylactic-glycolic acid (PLGA), and more preferably, is polyethylene glycol (PEG). In addition, derivatives thereof known in the art and derivatives easily prepared by a method known in the art may be included in the scope of the present invention.

The peptide linker which is used in the fusion protein obtained by a conventional inframe fusion method has drawbacks in that it is easily in-vivo cleaved by a proteolytic enzyme, and thus a sufficient effect of increasing the serum half-life of the active drug by a carrier cannot be obtained as expected. However, in the present invention, the polymer having resistance to the proteolytic enzyme can be used to maintain the serum half-life of the peptide being similar to that of the carrier. Therefore, any non-peptidyl polymer can be used without limitation, as long as it is a polymer having the aforementioned function, that is, a polymer having resistance to the in-vivo proteolytic enzyme. The non-peptidyl polymer has a molecular weight in the range of 1 to 100 kDa, and preferably of 1 to 20 kDa. The non-peptidyl polymer of the present invention, linked to the immunoglobulin Fc region, may be one polymer or a combination of different types of polymers.

The non-peptidyl polymer used in the present invention has a reactive group capable of binding to the immunoglobulin Fc region and protein drug. The non-peptidyl polymer has a reactive group at both ends, which is preferably selected from the group consisting of a reactive aldehyde, a propionaldehyde, a butyraldehyde, a maleimide and a succinimide derivative. The succinimide derivative may be succinimidyl propionate, hydroxy succinimidyl, succinimidyl carboxymethyl, or succinimidyl carbonate. In particular, when the non-peptidyl polymer has a reactive aldehyde group at both ends thereof, it is effective in linking at both ends with a physiologically active polypeptide and an immunoglobulin with minimal non-specific reactions. A final product generated by reductive alkylation by an aldehyde bond is much more stable than that linked by an amide bond. The aldehyde reactive group selectively binds to an N-terminus at a low pH, and binds to a lysine residue to form a covalent bond at a high pH, such as pH 9.0. The reactive groups at both ends of the non-peptidyl polymer may be the same or different. For example, the non-peptidyl polymer may possess a maleimide group at one end, and an aldehyde group, a propionaldehyde group or a butyraldehyde group at the other end. When a polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used so as to prepare the long acting insulin conjugate of the present invention. Preferably, the non-peptidyl polymer may be linked at the N-terminus of the beta chain of insulin.

The insulin of the present invention may be modified with a non-peptidyl polymer.

Actually, PEG (polyethylene glycol) modification for preventing hypoglycemia and improving duration of efficacy makes the titer of the physiological active peptide significantly low. However, this disadvantage becomes an advantage in the development of long-acting insulin conjugates using immunoglobulin fragments. Thus, PEG-modified insulin may be linked to the immunoglobulin Fc region via the non-peptidyl polymer. The non-peptidyl polymer used in the insulin modification may be selected from the group consisting of polyethylene glycol, polypropylene glycol, ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof, and preferably, polyethylene glycol. PEG modification in the PEG-modified insulin is characterized in that PEG selectively binds to the N-terminus of the alpha chain or to a particular lysine residue of the beta chain of insulin. The PEG modifying insulin preferably includes reactive aldehyde and succinyl groups at its ends, and more preferably, a reactive succinyl group.

The preparation method and efficacy of the long-acting insulin conjugate of the present invention is described in detail in Korean Patent Application Nos. 2010-0054068, 2010-0054067, and 2011-0030868. In one Example of the present invention, mono-PEGylation was performed at the N-terminus of immunoglobulin Fc region, and phenylalanine at position 1 of the beta chain of insulin was modified therewith to prepare the long-acting insulin conjugate (Example 1).

As used herein, the term "long-acting insulinotropic peptide conjugate" means an insulinotropic peptide linked with the immunoglobulin Fc region via the non-peptidyl linker.

In the present invention, "insulinotropic peptide" means a peptide that retains the function of releasing insulin, and stimulates synthesis or expression of insulin in the beta cells of the pancreas. Preferably, the insulinotropic peptide is GLP (Glucagon like peptide)-1, exendin-3, or exendin-4, but is not limited thereto. The insulinotropic peptide includes native insulinotropic peptides, precursors thereof, agonists thereof, derivatives thereof, fragments thereof, and variants thereof.

The insulinotropic peptide derivative of the present invention may include a desamino-histidyl derivative where the N-terminal amino group of insulinotropic peptide is deleted, beta-hydroxy imidazopropionyl-derivative where the amino group is substituted with a hydroxyl group, dimethyl-histidyl derivative where the amino group is modified with two methyl groups, beta-carboxyimidazopropionyl-derivative where the N-terminal amino group is substituted with a carboxyl group, or an imidazoacetyl-derivative where the alpha carbon of the N-terminal histidine residue is deleted to remain only the imidazoacetyl group and thus the positive charge of the amino group is removed, and other N-terminal amino group-modified derivatives are included within the scope of the present invention.

In the present invention, the insulinotropic peptide derivative is more preferably an exendin-4 derivative having a chemically modified N-terminal amino (or amine) group or amino acid residue, even more preferably an exendin-4 derivative which is prepared by removing or substituting the alpha amino group present in the alpha carbon of the N-terminal His1 residue of exendin-4 or by removing or substituting the alpha carbon. Still more preferably, desamino-histidyl-exendin-4 (DA-Exendin-4) with removal of the N-terminal amino group, beta-hydroxy imidazopropyl-exendin-4 (HY-exendin-4) prepared by substitution of the amino group with a hydroxyl group, beta-carboxy imidazopropyl-exendin-4 (CX-exendin-4) prepared by substitution of the amino group with a carboxyl group, dimethyl-histidyl-exendin-4 (DM-exendin-4) prepared by modification of the amino group with two methyl residues, or imidazo-acetyl-exendin-4 (CA-exendin-4) with removal of alpha carbon of N-terminal histidine residue.

GLP-1 is a hormone secreted by the small intestine, and usually promotes biosynthesis and secretion of insulin, inhibits glucagon secretion, and promotes glucose uptake by the cells. In the small intestine, a glucagon precursor is decomposed into three peptides, that is, glucagon, GLP-1, and GLP-2. Here, the GLP-1 means GLP-1 (1-37), which is originally in the form having no insulinotropic function, but is then processed and converted into one in the activated GLP-1 (7-37) forms. The sequence of the GLP-1 (7-37) amino acid is as follows:

```
GLP-1(7-37)
                                        (SEQ ID NO. 3)
HAEGT FTSDV SSYLE GQAAK EFIAW LVKGR G
```

The term, "GLP-1 derivative" means a peptide which exhibits an amino acid sequence homology of at least 80% with that of GLP-1, may be in the chemically modified form, and exhibits an insulinotropic function of at least equivalent or more to that of GLP-1.

The term, "GLP-1 fragment" means one in the form in which one or more amino acids are added or deleted at an N-terminus or a C-terminus of a native GLP-1, in which the added amino acid is possibly a non-naturally occurring amino acid (e.g., D-type amino acid).

The term, "GLP-1 variant" means a peptide possessing an insulinotropic function, which has one or more amino acid sequences different from those of a native GLP-1.

Exendin-3 and the exendin-4 are insulinotropic peptides consisting of 39 amino acids, which have a 53% amino acid sequence homology with GLP-1. The amino acid sequences of the exendin-3 and the exendin-4 are as follows:

```
Exendin-3
                                        (SEQ ID NO. 4)
HSDGT FTSDL SKQME EEAVR LFIEW LKNGG PSSGA PPPS Exendin-4
                                        (SEQ ID NO. 5)
HGEGT FTSDL SKQME EEAVR LFIEW LKNGG PSSGA PPPS
```

The term, "exendin agonist" means a compound reacting with receptors in-vivo and having biological activity equivalent to that of exendin.

The term, "exendin derivative" means a peptide having at least 80% amino acid sequence homology with the native exendin, which may have some groups on the amino acid residue chemically substituted (e.g., alpha-methylation, alpha-hydroxylation), deleted (e.g., deamination), or modified (e.g., N-methylation), and has an insulinotropic function.

The term, "exendin fragment" means a fragment having one or more amino acids added or deleted at the N-terminus or the C-terminus of the native exendin, in which non-naturally occurring amino acids (for example, D-type amino acid) can be added, and has an insulinotropic function.

The term, "exendin variant" means a peptide having at least one amino acid sequence different from that of the native exendin, which has an insulinotropic function, and the exendin variant includes peptides prepared by substituting lysine at position 12 of exendin-4 with serine or arginine.

Each of the preparation methods for the exendin agonist, derivative, the fragment, and the variant can be used individually or in combination. For example, the present invention includes an insulinotropic peptide having an amino acid sequence having at least one different amino acid from those of the native insulinotropic peptide, and having the amino acid residue at the N-terminus deaminated.

In a specific embodiment, the native insulinotropic peptide and the modified insulinotropic peptide used in the present invention can be synthesized using a solid phase synthesis method, and most of the native peptides including a native insulinotropic peptide can be produced by a recombination technology.

The long-acting insulinotropic peptide conjugate used in the present invention means an insulinotropic peptide linked with an immunoglobulin fragment such as immunoglobulin Fc via a non-peptidyl linker. The non-peptidyl linker is the same as described above. The long-acting insulinotropic peptide conjugate is a conjugate using the immunoglobulin fragment as in the long-acting insulin conjugate, and maintains the conventional in-vivo activities of the insulinotropic peptide, such as promotion of synthesis and secretion of insulin, appetite control, weight loss, increase in the beta cell sensitivity to glucose in blood, promotion of beta cell proliferation, delayed gastric emptying, and glucagon suppression, and further remarkably increases the blood half-life of the insulinotropic peptide, and subsequently the in-vivo efficacy sustaining effect of the peptide. Thus, it is useful in the treatment of diabetes and obesity.

The type and preparation method of the long-acting insulinotropic peptide conjugate are described in detail in Korean Patent Application Nos. 2008-001479, 2008-0069234, and 2010-0047019.

In one Example of the present invention, lysine (Lys) of imidazo-acetyl exendin-4 (CA exendin-4) was modified with PEG, and the PEG-modified exendin-4 was linked to the immunoglobulin Fc to prepare a long-acting exendin-4 conjugate (Example 2).

The insulin and the insulinotropic peptide used in the present invention are linked with a carrier substance using the non-peptidyl polymer as a linker. The carrier substance useful in the present invention may be selected from the group consisting of an immunoglobulin Fc region, albumin, transferrin, and PEG, and preferably an immunoglobulin Fc region.

Each of the long-acting insulin conjugate and the insulinotropic peptide conjugate of the present invention is prepared by linking insulin or insulinotropic peptide with the immunoglobulin Fc region via the non-peptidyl linker, thereby showing sustainability and stability. In the present invention, the immunoglobulin Fc may be interchangeably used with immunoglobulin fragment.

Also, an Fc fragment is beneficial in terms of preparation, purification and yield of a complex with the Fc fragment because it has a small molecular weight relative to whole immunoglobulin molecules. Further, since the Fab region, which displays high non-homogeneity due to the difference in amino acid sequence between antibodies, is removed, the Fc fragment has greatly increased substance homogeneity and a low potential to induce serum antigenicity.

The term "immunoglobulin Fc region" as used herein, refers to a protein that contains the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, the immunoglobulin Fc region may be a fragment having a deletion in a relatively long portion of the amino acid sequence of CH2 and/or CH3. That is, the immunoglobulin Fc region of the present invention may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

The immunoglobulin Fc region of the present invention includes a native amino acid sequence, and a sequence derivative (mutant) thereof. An amino acid sequence derivative is a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification.

Also, other various derivatives are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC (antibody dependent cell mediated cytotoxicity) site. Techniques of preparing such sequence derivatives of the immunoglobulin Fc region are disclosed in WO 97/34631 and WO 96/32478.

Amino acid exchanges in proteins and peptides, which do not generally alter the activity of the proteins or peptides, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. In addition, the Fc region, if desired, may be modified by phosphorylation, sulfation, acrylation, glycosylation, methylation, farnesylation, acetylation, amidation, and the like.

The aforementioned Fc derivatives are derivatives that have a biological activity identical to the Fc region of the present invention or improved structural stability, for example, against heat, pH, or the like.

In addition, these Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)$_2$ fragments. These fragments may be subjected, for example, to size exclusion chromatography to isolate Fc or pF'c. Preferably, a human-derived Fc region is a recombinant immunoglobulin Fc region that is obtained from a microorganism.

In addition, the immunoglobulin Fc region of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the C1q part of the first complement component C1 and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable to the object of the present invention as a drug carrier.

As used herein, the term "deglycosylation" refers to enzymatically removing sugar moieties from an Fc region, and the term "aglycosylation" means that an Fc region is produced in an unglycosylated form by a prokaryote, preferably *E. coli*.

Meanwhile, the immunoglobulin Fc region may be derived from humans or other animals including cows, goats, pigs, mice, rabbits, hamsters, rats and guinea pigs, and preferably from humans.

In addition, the immunoglobulin Fc region may be an Fc region that is derived from IgG, IgA, IgD, IgE and IgM, or that is made by combinations thereof or hybrids thereof. Preferably, it is derived from IgG or IgM, which are among the most abundant proteins in human blood, and most preferably from IgG, which is known to enhance the half-lives of ligand-binding proteins.

On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid", as used herein, means that sequences encoding two or more immunoglobulin Fc regions of different origin are present in a single-chain immunoglobulin Fc region. In the present invention, various types of hybrids are possible. That is, hybrid domains may be composed of one to four domains selected from the group consisting of CH1, CH2, CH3 and CH4 of IgG Fc, IgM Fc, IgA Fc, IgE Fc and IgD Fc, and may include the hinge region.

On the other hand, IgG is divided into IgG1, IgG2, IgG3 and IgG4 subclasses, and the present invention includes combinations and hybrids thereof. Preferred are the IgG2 and IgG4 subclasses, and most preferred is the Fc region of IgG4 rarely having effector functions such as CDC (complement dependent cytotoxicity).

That is, as the drug carrier of the present invention, the most preferable immunoglobulin Fc region is a human IgG4-derived non-glycosylated Fc region. The human-derived Fc region is more preferable than a non-human derived Fc region, which may act as an antigen in the human body and cause undesirable immune responses such as the production of a new antibody against the antigen.

The composition of the present invention is characterized by concurrent administration of the long-acting insulin conjugate and the long-acting insulinotropic peptide conjugate.

When the concurrent administration of the long-acting insulin conjugate and the long-acting insulinotropic peptide conjugate of the present invention is performed, the long-acting insulin conjugate acts on the insulin receptor and the long-acting insulinotropic peptide conjugate acts on the glucagon like peptide-1 receptor at the same time, so that the blood glucose level is decreased and a stable blood glucose level is maintained, compared to single administration thereof. The concurrent administration of the conjugates has the effects of reducing the risk of hypoglycemia and weight gain which can be induced by single administration of insulin, and also reduces the dose of the total insulin owing to the action of the insulinotropic peptide. The concurrent administration is also advantageous in that the dose of the insulinotropic peptide such as exendin-4 can also be reduced to prevent adverse effects such as nausea and vomiting caused by single administration of exendin-4. The use of long-acting insulin conjugate and the long-acting insulinotropic peptide conjugate remarkably increases the blood half-life and in-vivo duration of efficacy, so that the treatment frequency is reduced to improve quality of life in chronic patients that suffer from daily injections. Thus, it is very useful for the treatment of diabetes. Further, the pharmaceutical composition of the present invention shows excellent duration of in-vivo efficacy and titers, and the dose can be greatly reduced upon concurrent administration.

The long-acting insulin conjugate and the long-acting insulinotropic peptide conjugate may be administered simultaneously, sequentially or reversely, and may be administered simultaneously in a proper combination of effective doses. Preferably, the long-acting insulin conjugate and the long-acting insulinotropic peptide conjugate can be stored separately in individual containers, and then administered simultaneously, sequentially or reversely.

Further, the composition for concurrent administration of the present invention may be in a form of a therapeutic kit for diabetes that includes the long-acting insulin conjugate and the long-acting insulinotropic peptide conjugate in a single container or separately in individual containers. The kit may include a pharmaceutically acceptable carrier and an instruction manual.

Figure 1:
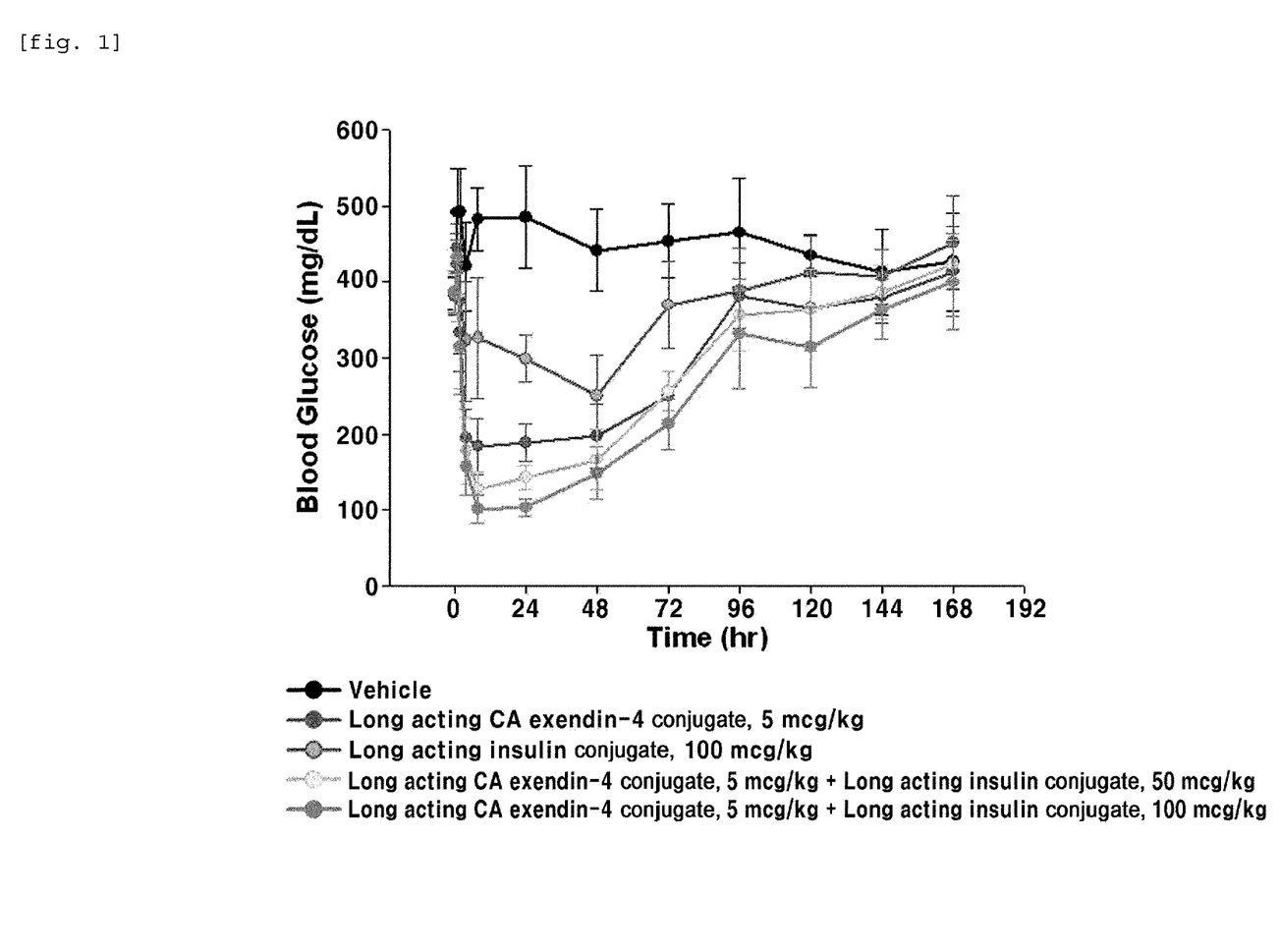
FIG. 1 is a graph showing the changes in blood glucose levels for a 7-day period after concurrent administration of the long-acting insulin conjugate and the long-acting exendin-4 conjugate to STZ (Streptozotocin)-induced diabetic mice.
Figure 2:
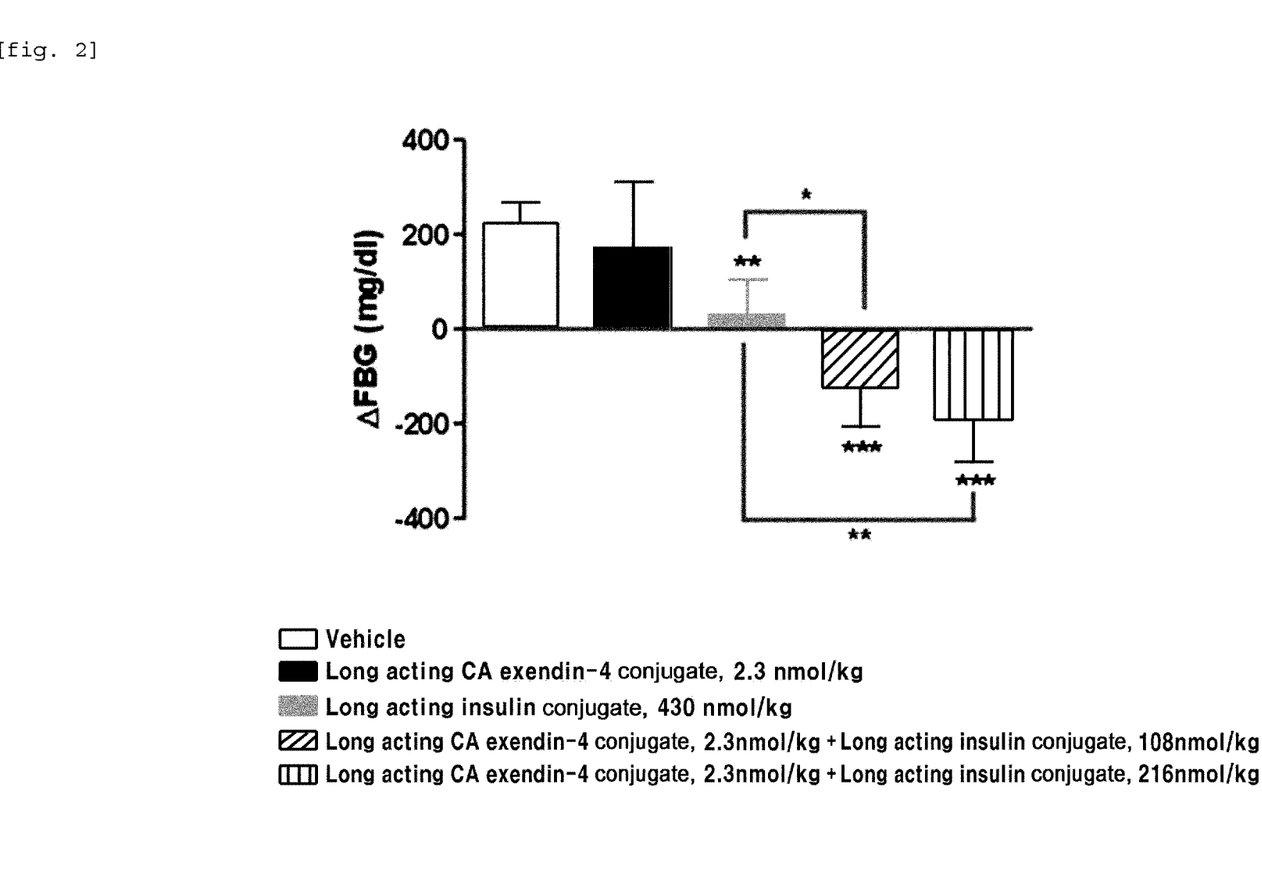
FIG. 2 is a graph showing the changes in fasting blood glucose ($\Delta$FBG) after concurrent administration of the long-acting insulin conjugate and the long-acting exendin-4 conjugate to db/db mice (* $P<0.05$,  $P<0.01$, * $P<0.001$ by Dunnet's MC test)
Figure 3:
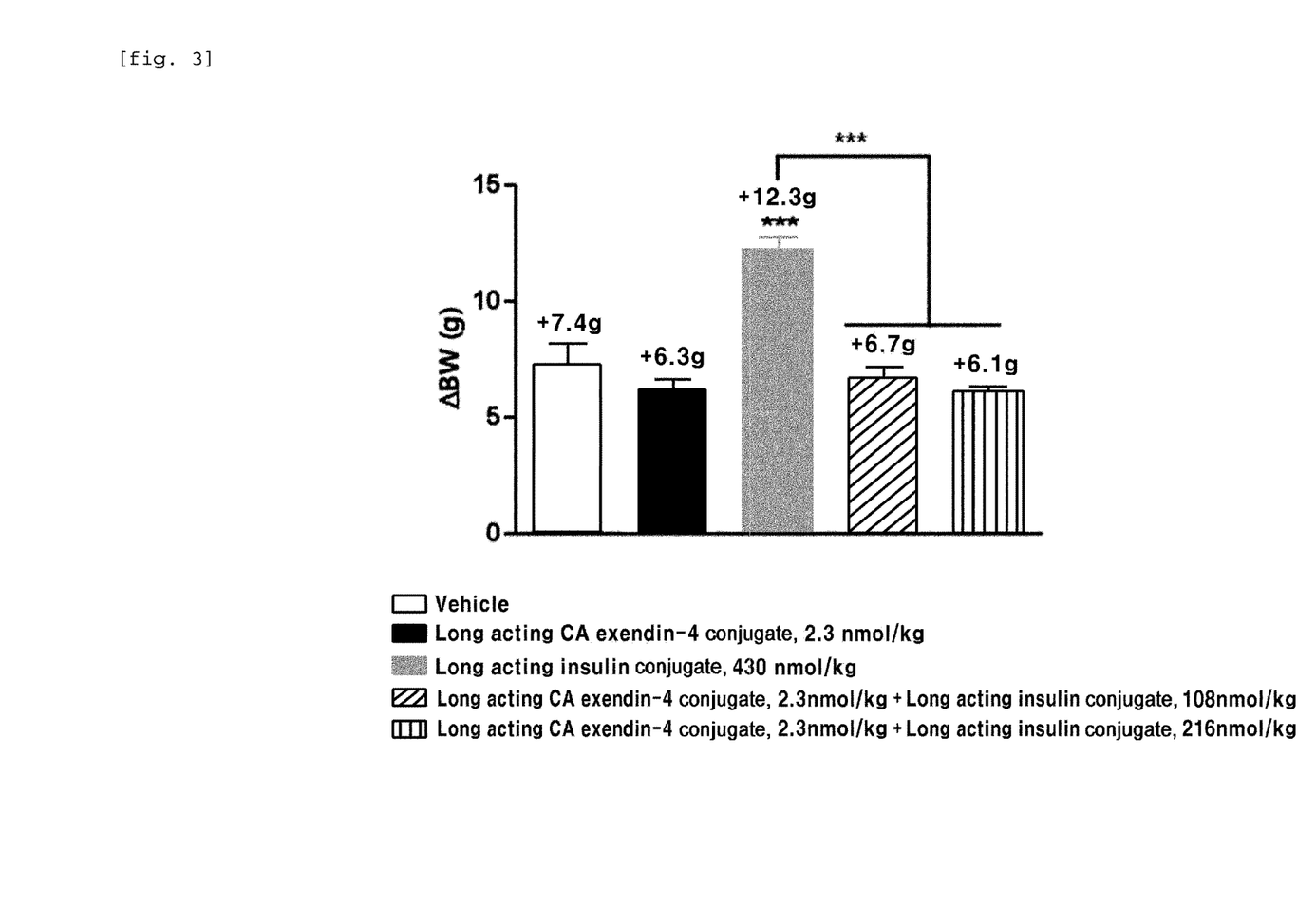
FIG. 3 is a graph showing the changes in body weight ($\Delta$BW) after concurrent administration of the long-acting insulin conjugate and the long-acting exendin-4 conjugate to db/db mice (* $P<0.05$,  $P<0.01$, * $P<0.001$ by Dunnet's MC test).

In one specific Example of the present invention, changes in the blood glucose levels were examined after concurrent administration of the long-acting insulin conjugate and the long-acting exendin-4 conjugate to STZ (Streptozotocin)-induced diabetic mice. As a result, concurrent administration of the conjugates showed a stable pattern in blood glucose levels, compared to single administrations (FIG. 1). The fasting blood glucose levels were compared before and after concurrent administration of the long-acting insulin conjugate and the long-acting exendin-4 conjugate in mouse models of type 2 diabetes once a week. As a result, concurrent administration showed excellent improvement in the blood glucose levels, compared to single administrations (FIG. 2). In addition, weight gain caused by insulin treatment was not observed, indicating that concurrent administration reduces the side effect of weight gain due to insulin (FIG. 3).

As used herein, the term "diabetes" means a metabolic disease caused by an abnormality in the secretion or function of insulin. Concurrent administration of the composition of the present invention to a subject is performed to control the blood glucose level, thereby treating diabetes.

As used herein, the term "prevention" means all of the actions by which the occurrence of diabetes is restrained or retarded by concurrent administration of the composition of the present invention, and the term "treatment" means all of the actions by which the symptoms of diabetes have taken a turn for the better or been modified favorably by concurrent administration of the composition of the present invention. The treatment of diabetes can be applied to any mammal that may have diabetes, and examples thereof include humans and primates as well as livestock such as cattle, pig, sheep, horse, dog, and cat without limitation, and preferably human.

As used herein, the term "administration" means introduction of a predetermined amount of a substance into a patient by a certain suitable method. The composition may be administered via any of the common routes, as long as it is able to reach a desired tissue. A variety of modes of administration are contemplated, including intraperitoneal, intravenous, intramuscular, subcutaneous, intradermal, oral, topical, intranasal, intrapulmonary and intrarectal, but the present invention is not limited to these exemplified modes of administration. However, since peptides are digested upon oral administration, active ingredients of a composition for oral administration should be coated or formulated for protection against degradation in the stomach. Preferably, the multimer may be administered in an injectable form. In addition, the pharmaceutical composition may be administered using a certain apparatus capable of transporting the active ingredients into a target cell.

Further, the pharmaceutical composition of the present invention can be determined by several related factors including the types of diseases to be treated, administration routes, the patient's age, gender, weight and severity of the illness, as well as by the types of the drug used as an active component.

Further, the pharmaceutical composition of the present invention may include a pharmaceutically acceptable carrier. As used herein, the term "pharmaceutically acceptable carrier" refers to a carrier or diluent that does not cause significant irritation to an organism and does not abrogate the biological activity and properties of the administered compound. For oral administration, the pharmaceutically acceptable carrier may include a binder, a lubricant, a disintegrant, an excipient, a solubilizer, a dispersing agent, a stabilizer, a suspending agent, a coloring agent, and a flavor. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into a unit dosage form, such as a multi-dose container or an ampule as a single-dose dosage form. The pharmaceutical composition may be also formulated into solutions, suspensions, tablets, pills, capsules and long-acting preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavors, and antiseptics.

In another aspect, the present invention provides a method for preventing or treating diabetes, comprising the step of administering the composition including the long-acting insulin conjugate and the long-acting insulinotropic peptide conjugate to a subject having diabetes or at risk of having diabetes.

The administration step may be performed by concurrent administration of the long-acting insulin conjugate and the long-acting insulinotropic peptide conjugate, but is not limited to, simultaneously, sequentially or reversely, and the long-acting insulin conjugate and the long-acting insulinotropic peptide conjugate are administered simultaneously in a proper combination of effective doses.

Even though administered once a week, the composition including both of the long-acting insulin conjugate and the long-acting insulinotropic peptide conjugate of the present invention shows excellent improvement in the blood glucose levels and causes no side effect of weight gain, and thus can be used for the prevention or treatment of diabetes.

In another aspect, the present invention provides a pharmaceutical composition for the prevention or treatment of diabetes comprising a long-acting insulin conjugate and an insulinotropic peptide.

The long-acting insulin conjugate and the insulintropic peptide is the same as described above. The long-acting insulin conjugate may be administered concurrently with the insulinotropic peptide such as GLP-1 agonists (for example, Exenatide, Liraglutide or Lixisenatide).

In another aspect, the present invention provides a pharmaceutical composition for the prevention or treatment of diabetes comprising insulin and a long-acting insulinotropic peptide conjugate.

The insulin and the long-acting insulintropic peptide conjugate is the same as described above. The long-acting insulinotropic peptide conjugate may be administered concurrently with the insulin such as the native insulin, the insulin derivatives or the basal insulin.

MODE FOR INVENTION

Hereinafter, the present invention will be described in more detail with reference to the following Examples. However, these Examples are for illustrative purposes only, and the invention is not intended to be limited thereby.

Example 1: Preparation of Long-Acting Insulin Conjugate

For PEGylation of the N-terminus of immunoglobulin Fc region with 5K PropionALD (3) PEG (PEG with three propylaldehyde groups, NOF, Japan), the immunoglobulin Fc region and PEG were reacted at a molar ratio of 1:2 with the immunoglobulin Fc concentration of 10 mg/mL at 4° C. for 4.5 h. At this time, the reaction was conducted in a 100 mM potassium phosphate (pH 6.0), and a reducing agent, 20 mM SCB (NaCNBH$_3$) was added thereto. The mono-PEGylated immunoglobulin Fc was purified from the reaction mixture using a SOURCE 15Q (GE Healthcare) purification column.

In order to prepare an insulin-PEG-immunoglobulin Fc conjugate having 90% or more modification of phenylalanine (B1F) at position 1 of the beta chain of insulin, the mono-PEGylated immunoglobulin Fc and insulin were prepared at a molar ratio of 4:1 and at the total protein concentration of 20 mg/mL, and reacted with each other at 4° C. for 20 h. 100 mM potassium phosphate (pH 6.0) was used as a reaction solution, and 20 mM SCB was added thereto as a reducing agent. After termination of the reaction, primary purification of the reaction mixture was performed using a Source 15Q purification column. Then, second purification was performed using a Source 15ISO purification column to obtain an insulin-PEG-immunoglobulin Fc conjugate.

Example 2: Preparation of Long-Acting Exendin-4 Conjugate 3.4 k PropionALD (2) PEG was reacted with the lysine (Lys) of CA exendin-4 using imidazo-acetyl exendin-4 (CA exendin-4, AP, USA). Among the two Lys isomer peaks, the last isomer peak (positional isomer of Lys27), which has more reaction and which is easily distinguishable from the N-terminal isomer peaks, was used for the coupling reaction.

The reaction was performed at a molar ratio of peptide: immunoglobulin Fc of 1:8, and a total concentration of proteins of 60 mg/mL at 4° C. for 20 h. The reaction was performed in a solution of 100 mM K-P (pH 6.0), and 20 mM SCB was added as a reducing agent. The coupling reaction solution was purified through two purification columns. First, SOURCE Q (XK 16 mL, Amersham Biosciences) was used to remove a large amount of immunoglobulin Fc which had not participated in the coupling reaction. Using 20 mM. Tris (pH 7.5) and 1 M NaCl with salt gradients, the immunoglobulin Fc having relatively weak binding power was eluted earlier, and then the exendin-4-immunoglobulin Fc was eluted. Through this first purification procedure, the immunoglobulin Fc was removed to some degree, but since the immunoglobulin Fc and the exendin-4-immunoglobulin Fc have similar binding powers to each other in the ion exchange column, they could not be completely separated from each other. Accordingly, secondary purification was performed using hydrophobicity of each of two materials. Using 20 mM Tris (pH7.5) and 1.5 M ammonium sulfate in SOURCE ISO (HR 16 mL, AmershamBiosciences), the first purified samples were coupled, and the sample was eluted with gradually reducing the concentration of ammonium sulfate. In the HIC Column, the immunoglobulin Fc having weak binding power was eluted earlier, and then the exendin-4-immunoglobulin Fc sample having strong binding power was eluted. Since they have prominently different hydrophobicity, they can be more easily separated from each other than in the ion exchange column.

Column: SOURCE Q (XK 16 mL, Amersham Biosciences)

Flow rate: 2.0 mL/min

Gradient: A0→25% 70 min B (A: 20 mM Tris pH7.5, B: A+1 M NaCl)

Column: SOURCE ISO (HR 16 mL, Amersham Biosciences)

Flow rate: 7.0 mL/min

Gradient: B 100→0% 60 min B (A: 20 mM Tris pH7.5, B: A+1.5M ammonium sulfate)

Example 3: Efficacy Test on Concurrent Administration of Long-Acting Insulin Conjugate and Long-Acting Exendin-4 Conjugate in STZ (Streptozotocin)-Induced Diabetes In order to perform in vivo efficacy test on administration of the compositions including the long-acting insulin conjugate and the long-acting exendin-4 conjugate prepared in Examples 1 and 2 or concurrent administration of the long-acting insulin conjugate and the long-acting exendin-4 conjugate, changes in the blood glucose levels were examined using STZ (Streptozotocin)-induced diabetic mice.

Diabetes was induced in 7-week old C57BL/6 mice fasted for 16 h by intraperitoneal injection of STZ (50 mg/kg, 1 mg/mL) in 10 mM citrate buffer (pH 4.5) for 5 consecutive days. After 2 days, 1-2 drops of blood was taken from the tail vein using a 26 G syringe, and the blood glucose was measured using a glucometer (OneTouch Ultra, LifeScan, Inc., USA). Diabetes induction was determined by the measured blood glucose (350-600 mg/dL).

Diabetes-induced mice were divided into five groups of five mice each: G1, G2, G3, G4 and G5.

The groups were divided into a non-treated control group (Vehicle), a long-acting exendin-4 conjugate-treated group (5 mcg/kg), a long-acting insulin conjugate-treated group (100 mcg/kg), a long-acting exendin-4 conjugate (5 mcg/kg) and long-acting insulin conjugate (50 mcg/kg)-treated group, and a long-acting exendin-4 conjugate (5 mcg/kg) and long-acting insulin conjugate (100 mcg/kg)-treated group. After treatment of the above test materials, changes in the blood glucose levels were measured in each group every day.

As a result, the concurrent treatment of the long-acting insulin conjugate and the long-acting exendin-4 conjugate showed a stable blood glucose level and a sustained hypoglycemic effect (FIG. 1), and showed remarkably lower blood glucose levels, compared to single administration of the long-acting exendin-4 conjugate or the long-acting insulin conjugate.

These results suggest that the concurrent administration of the long-acting insulin conjugate and the long-acting exendin-4 conjugate of the present invention shows a stable and sustained hypoglycemic effect, and thus remarkably reduces the administration dose, leading to reduction of side effects of exendin-4 such as vomiting and nausea and prevention of weight gain caused by insulin treatment.

Example 4: Changes in Fasting Blood Glucose (ΔFBG) and Body Weight (ΔBW) by Concurrent Administration of Long-Acting Insulin Conjugate and Long-Acting Exendin-4 Conjugate In order to perform in vivo efficacy test on administration of the compositions including the long-acting insulin conjugate and the long-acting exendin-4 conjugate prepared in Examples 1 and 2 or concurrent administration of the long-acting insulin conjugate and the long-acting exendin-4 conjugate, the improvement of the blood glucose levels and inhibition of weight gain were examined using type 2 diabetic db/db mouse.

Type 2 diabetic db/db mice were divided into single and concurrent administration groups of the long-acting insulin conjugate and the long-acting exendin-4 conjugate. Single administration groups were treated with 430 nmol/kg of the long-acting insulin conjugate and 2.3 nmol/kg of the long-acting exendin-4 conjugate by subcutaneous injection once a week, respectively. Concurrent administration groups were treated with 108 nmol/kg and 216 nmol/kg of the long-acting insulin conjugate and 2.3 nmol/kg of the long-acting exendin-4 conjugate by subcutaneous injection once a week. The test was performed for 28 days, and the animals were fasted for 8 h prior to the initial drug treatment and on the last day of the experiment, and then changes in fasting blood glucose (ΔFBG) and body weight (ΔBW) prior to the drug treatment and on the last day of the experiment were determined and calculated as final test items.

The measurement results of ΔFBG and ΔBW showed that concurrent administration of the long-acting insulin conjugate and the long-acting exendin-4 conjugate once a week showed excellent effects of improving the blood glucose level (FIG. 2) and inhibiting weight gain (FIG. 3) at a quarter dose of insulin (108 nmol/kg), compared to single administration of the long-acting insulin conjugate. These results shows that concurrent administration of the long-acting insulin conjugate and the long-acting CA exendin-4 conjugate has the advantages of reducing the risk of hypoglycemia and inhibiting weight gain by the reduction in the dose of insulin, indicating that even though the concurrent administration was performed once a week, it shows an excellent hypoglycemic effect, compared to daily injections of insulin and GLP-1 agonist, and also shows excellent blood glucose control greater than single administrations, and it reduces the demand for insulin, thereby reducing the risk of hypoglycemia and weight gain caused by insulin.

These results support that, even though administered once a week, the composition including the long-acting insulin conjugate and the long-acting exendin-4 conjugate of the present invention shows excellent blood glucose control and does not induce weight gain caused by insulin treatment while it remarkably reduces the side effects caused by single administrations of the known insulin peptide and exendin-4.

The invention claimed is:

1. A pharmaceutical composition comprising a long-acting insulin conjugate and a long-acting insulinotropic peptide conjugate, wherein each of the long-acting insulin conjugate and the long-acting insulinotropic peptide conjugate is prepared by linking an insulin or an insulinotropic peptide with an immunoglobulin Fc region via a non-peptidyl linker selected from the group consisting of polyethylene glycol, polypropylene glycol, ethylene glycol-propylene glycol copolymer, polyoxyethylated polyol, polyvinyl alcohol, dextran, polyvinyl ethyl ether, a biodegradable polymer, a lipid polymer, chitin, hyaluronic acid, and a combination thereof;

wherein the insulinotropic peptide is selected from the group consisting of glucagon like peptide-1, exendin-3, exendin-4, an exendin-4 derivative prepared by deleting N-terminal amine group, an exendin-4 derivative prepared by substituting N-terminal amine group with hydroxyl group, an exendin-4 derivative prepared by modifying N-terminal amine group with dimethyl group, and an exendin-4 derivative prepared by deleting α-carbon of the first amino acid of exendin-4;

wherein said insulin of the long-acting insulin conjugate is selected from the group consisting of the following (i)-(v):

(i) a native insulin comprising a first peptide of SEQ ID NO: 1 and a second peptide of SEQ ID NO: 2;

(ii) a basal insulin;

(iii) an insulin variant which comprises a first peptide of SEQ ID NO: 1 and a second peptide of SEQ ID NO: 2, in which one or more of the amino acid residues of SEQ ID NO: 1 and/or SEQ ID NO: 2 is different from the amino acid sequence of the native insulin (i) by way of substitution, deletion, modification, and/or addition, wherein the insulin variant retains a function of controlling blood glucose level in a body of subject to which said insulin variant is administered;

(iv) an insulin derivative peptide which has at least 80% amino acid sequence identity to the native insulin (i), wherein a chemical group of one or more of the amino acid residues of SEQ ID NO: 1 and/or SEQ ID NO: 2 is chemically modified, and wherein the insulin derivative peptide retains a function of controlling blood glucose level in a body of subject to which said insulin derivative peptide is administered; or (v) a fragment of the native insulin (i), said fragment having one or more amino acids deleted at the N-terminus or the C-terminus of the native insulin (i) or having a non-naturally occurring amino acid, wherein the fragment retains a function of controlling blood glucose level in a body of subject to which said fragment is administered; and wherein the non-peptidyl linker has a molecular weight in a range from 1 kDa to 100 kDa.

2. The composition according to claim 1, wherein the insulin is modified with a non-peptidyl polymer.

3. The composition according to claim 2, wherein the non-peptidyl polymer is selected from the group consisting of polyethylene glycol, polypropylene glycol, ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof.

4. The composition according to claim 1, wherein the immunoglobulin Fc region is aglycosylated.

5. The composition according to claim 1, wherein the immunoglobulin Fc region is composed of one to four domains selected from the group consisting of CH1, CH2, CH3 and CH4 domains.

6. The composition according to claim 1, wherein the immunoglobulin Fc region further includes a hinge region.

7. The composition according to claim 1, wherein the immunoglobulin Fc region is an Fc region derived from IgG, IgA, IgD, IgE, or IgM.

8. The composition according to claim 1, wherein the immunoglobulin Fc region is composed of domains having different origins, wherein the origin is selected from the group consisting of IgG, IgA, IgD, IgE, and IgM.

9. The composition according to claim 1, wherein the immunoglobulin Fc region is a dimer or a multimer composed of single-chain immunoglobulins of the same origin.

10. The composition according to claim 1, further comprising a pharmaceutically acceptable carrier.

11. The composition according to claim 1, wherein the long-acting insulin conjugate and the long-acting insulinotropic peptide conjugate are administered simultaneously, sequentially, or reversely.

12. The composition according to claim 1, wherein the basal insulin is insulin detemir, insulin glargine, or insulin deglude.

13. A method for treating diabetes, comprising the step of administering the composition of claim 1 to a subject having diabetes or at risk of having diabetes.

14. The method according to claim 13, wherein the administration step is performed by concurrent administration of the long-acting insulin conjugate and the long-acting insulinotropic peptide conjugate.

15. The method according to claim 14, wherein the concurrent administration is performed by administrating the long-acting insulin conjugate and the long-acting insulinotropic peptide conjugate simultaneously, sequentially, or reversely.

* * * * *